United States Patent [19]

Muller et al.

[11] Patent Number: 4,936,861
[45] Date of Patent: Jun. 26, 1990

[54] ACETABULAR CUP PROSTHESIS

[75] Inventors: Maurice E. Muller, Bern; Otto Frey, Winterthur; Roland Willi, Stadel, all of Switzerland

[73] Assignees: Sulzer Brothers Limited, Winterthur; Protek AG, Berne, both of Switzerland

[21] Appl. No.: 255,051

[22] Filed: Oct. 7, 1988

[30] Foreign Application Priority Data

Oct. 28, 1987 [CH] Switzerland ............ 4225/87

[51] Int. Cl.$^5$ ............................................. A61F 2/34
[52] U.S. Cl. ............................................. 623/22
[58] Field of Search ................ 623/16, 18, 20, 21, 623/22, 23

[56] References Cited

U.S. PATENT DOCUMENTS 4,650,491 3/1987 Parchinski ............... 623/22
4,666,450 3/1987 Kenna ............... 623/22
4,792,337 12/1988 Muller ............... 623/22

FOREIGN PATENT DOCUMENTS 3341723 11/1983 Fed. Rep. of Germany ........ 623/22

Primary Examiner—Richard J. Apley
Assistant Examiner—David J. Isabella
Attorney, Agent, or Firm—Kenyon & Kenyon

[57] ABSTRACT

The plastic cup-comprising member and the hemispherical shell of the two-part acetabular cup prosthesis are secured relative to one another in snap-fitted manner. The plastic member is centered and guided during pressing-in via a centering pin and concentric annular web on the plastic member. The annular web is also locally deformable so as to deform against a screw head during pressing-in without the annular web losing its centering guiding action.

7 Claims, 1 Drawing Sheet

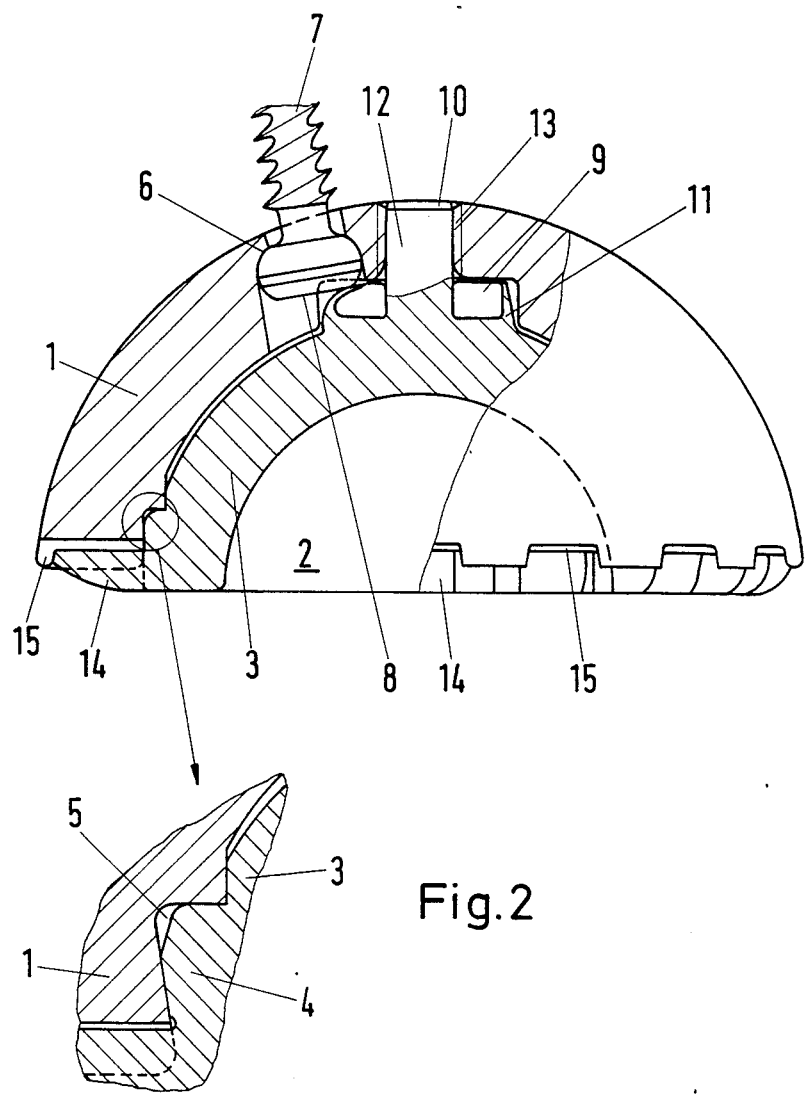

ACETABULAR CUP PROSTHESIS

This invention relates to an acetabular cup prosthesis. More particularly, this invention relates to two-part acetabular cup prosthesis.

Heretofore, various types of two-part acetabular cup prosthesis have been known for implanting in a pelvic bone. Generally, this type of prosthesis has a fixing member in the form of a hemispherical shell which can be fixed in the pelvis by bone screws as well as a plastic member which can be secured by a snap-fitted connection in the hemispherical shell. Usually, the plastic member has a cup for receiving the head of a joint. During assembly, the plastic member is fitted into the hemispherical shell by being pressed in axially of the shell.

As described in Swiss Patent No. 668-180, the primary anchorage for such a prosthesis is by means of a number of bone screws threaded into the pelvis in different directions. However, if, for example, the axes cf the screws differ considerably in their direction from a physical radius of the hemispherical shell, the screw heads may project into the hollow interior of the hemispherical shell which receives the plastic cup-comprising member. Thus, when the plastic member and the hemispherical shell are secured relative to each other by a snap fastening, a projecting screw head may cause difficulties in fixing the plastic member in place, particularly when the plastic member has a cylindrical guide projecting from an outside surface such as described in European Patent Application No. 0245527 and the projecting screw head is disposed near the guide.

Accordingly, it is an object of the invention to avoid any difficulties provided by projecting bone screws in a two-part acetabular cup prosthesis.

It is another object of the invention to permit a snap fitting of a plastic member in a hemispherical shell without hinderance by bone screws.

Briefly, the invention provides an acetabular cup prosthesis which is comprised of a hemispherical shell and a plastic member.

The hemispherical shell is formed with a plurality of openings for passage of bone screws therethrough in order to anchor the shell in a pelvis as well as a centrally disposed guide or recess.

The plastic member is formed with a cup for receiving a head of a joint and means for snap-fitting of the member coaxially in the shell. In addition, the plastic member is provided with a cylindrical cam in the form of a thin-walled annular web which extends into the guide or recess of the shell coaxially. This web is locally deformable during fitting of the plastic member into the shell so as to deform against a bone screw projecting towards the plastic member. That is, when the plastic member is pressed into the hemispherical shell, the thin walled web deforms locally at the place of the projecting screw head without excessive impairment of the servicability of the annular web.

The snap-fitting in of the plastic member in the hemispherical shell can be facilitated if the plastic member has a centering pin concentric to the annular web at the apex region for reception in a central bore of the hemispherical shell.

The construction of the acetabular cup prosthesis is particularly advantageous where the openings for the bone screws in the hemispherical shell are concentrated near a main loading direction between two meridian circles of the hemispherical shell.

The plastic member may be made in known manner of a plastic which is conventional in the implant art, for example, polyethylene. The hemispherical shell, on the other hand, may be made of a metal which is compatible with the human body, such as pure titanium or a titanium alloy.

These and other objects and advantages of the invention will become more apparent from the following detailed description taken in conjunction with the accompanying drawings wherein:

FIG. 1 illustrates a side elevational view, partly in section, of an acetabular cup prosthesis constructed in accordance with the invention; and FIG. 2 illustrates a detail of FIG. 1 to an enlarged scale of a snap-fitting relationship between the hemispherical shell and plastic member of the prosthesis.

Referring to FIG. 1, the two-part acetabular cup prosthesis includes a hemispherical shell 1 of metal which defines a fixing member and a plastic member 3 having an acetabular cup 2 for receiving the head of a joint (not shown). As indicated in FIG. 2, the plastic member 3 is snap-fitted into the shell 1. To this end, the exterior surface of the plastic member 3 is provided with a means in the form of an annular projection 4 for snap fitting of the member 3 coaxially in a corresponding groove 5 in the hollow interior of the hemispherical shell 1. As FIG. 2 illustrates, the projection 4 and the groove 5 have conical flanks which widen in the direction in which the plastic member 3 is snap-fitted into the shell 1.

For primary fixing, the hemispherical shell 1 is provided with a plurality of openings 6 for passage of bone screws 7 (only one of which is shown for simplicity) therethrough to anchor the shell 1 in a pelvis. The shell 1 is also provided with a centrally disposed guide in the form of a cylindrical recess 9 as well as with a central bore 10 which is provided with a screw thread 13 for connecting the shell I to a setting instrument (not shown).

As indicated in FIG. 1, should the axis of the screw 7 depart from a "radial" direction of the shell 1, the head 8 of the screw 7 extends into the cylindrical recess 9.

The plastic member 3 is also provided with an annular cam in the form of a thin-walled annular web 11 with a longitudinal extent extending coaxially of the shell 1 and a centering pin 12 which is concentric with the annular web 11 and which is disposed in the apex zone of the member 3.

The cylindrical recess 9 and the bore 10 are operative in cooperation with the annular web 11 and the (centering pin 12 to center and guide the plastic member 3 during snap fitting into the hemispherical shell 1. As indicated, the centering pin 12 is received in the central bore 10 while the annular web 11 is coaxially received within the guide or recess 9.

The thin-walled annular web 11 is characterized in being locally deformable during fitting of the plastic member 3 into the shell 1. That is, the portion of the web 11 which is aligned with the opening 6 from which the screw head 8 projects is deformable against the bone screw 7 upon fitting of the plastic member 3 into the shell 1.

As indicated in FIG. 1, the edge of the plastic member 3 has a ring of radially outwardly extending projections 14 at the equator which engage in grooves 15 in the equatorial plane of the hemispherical shell 1 The projections 14 and grooves 15 cooperate to form an intraoperative adjusting means for securing the plastic member 3 in the shell 1 in nonrotatable manner. This adjustability arises because the projections 14 and grooves 15 are distributed at equiangular "intervals" around the periphery of the plastic member 3 and the shell 1.

The invention thus provides a two-part acetabular cup prosthesis wherein a plastic member can be snap-fitted into a hemispherical shell without hinderance from the bone screws which fix the shell in a pelvis.

The invention further provides a plastic member for an acetabular cup prosthesis having a centering cam in the form of a thin-walled annular web which can be deformed locally by a hard projecting screw head without the annular web losing the centering guiding action.

What is claimed is:

1. An acetabular cup prosthesis comprising
    a hemispherical shell having a plurality of openings for passage of bone screws therethrough to anchor said shell in a pelvis and a centrally disposed guide; and
    a plastic member having a cup for receiving a head of a joint, means for snap-fitting of said member coaxially in said shell and a thin-walled annular web extending into said guide of said shell coaxially of said shell with a longitudinal extent extending, said web being locally deformable during fitting of said member into said shell.

2. An acetabular cup prosthesis as set forth in claim 1 wherein said plastic member has a centering pin concentric to said annular web and said shell has a central bore receiving said pin.

3. An acetabular cup prosthesis as set forth in claim 1 wherein said openings in said shell are concentrated near a main loading direction between two meridian circles of said shell.

4. An acetabular cup prosthesis comprising
    a hemispherical shell having a centrally disposed recess and a plurality of openings for passage of bone screws therethrough, at least one of said openings being in communication with said recess; and
    a plastic member having a cup for receiving a joint head, means for snap-fitting of said member coaxially in said shell and a thin-walled annular web with a longitudinal extent extending into said shell with a portion of said web aligned with said one opening, said web portion being deformable against a bone screw projecting from said one opening upon fitting of said member in said shell.

5. An acetabular cup prosthesis as set forth in claim 4 wherein said plastic member has a centering pin concentric to said annular web and said shell has a central bore receiving said pin.

6. An acetabular cup prosthesis comprising
    a hemispherical shell having a centrally disposed cylindrical recess and a plurality of openings for passage of bone screws therethrough, at least one of said openings being in communication with said recess; and
    a plastic member having a cup for receiving a joint head, means for snap-fitting of said member coaxially in said shell and a thin-walled annular web with a longitudinal extent extending coaxially into said recess of said shell with a portion of said web aligned with one of said passages, said web portion being deformable against a bone screw projecting from said one passage upon fitting of said member in said shell.

7. An acetabular cup prosthesis as set forth in claim 6 wherein said plastic member has a centering pin concentric to said annular web and said shell has a central bore receiving said pin.

* * * * *

UNITED STATES PATENT AND TRADEMARK OFFICE
CERTIFICATE OF CORRECTION

PATENT NO. : 4,936,861

DATED : June 26, 1990

INVENTOR(S) : Maurice E. Muller, et al.

It is certified that error appears in the above-identified patent and that said Letters Patent is hereby corrected as shown below:

```
Column 2, line 52 change "(center-" to -- center --
Column 2, line 68 change "1 The" to -1. The-
Column 3, line 27 after "shell" insert -with a longitudinal
extent extending-
Column 3, line 28 cancel "with ... extending"
```

Signed and Sealed this

Eleventh Day of February, 1992

Attest:

HARRY F. MANBECK, JR.

*Attesting Officer*     *Commissioner of Patents and Trademarks*